United States Patent [19]

Olbrich

[11] Patent Number: 5,073,662

[45] Date of Patent: Dec. 17, 1991

[54] CATALYST AND PROCESS FOR DEHYDROGENATION AND DEHYDROCYCLIZATION

[75] Inventor: Michael E. Olbrich, Naperville, Ill.

[73] Assignee: Phillips Petroleum Company, Bartlesville, Okla.

[21] Appl. No.: 513,407

[22] Filed: Apr. 23, 1990

[51] Int. Cl.[5] .............................................. C07C 5/333
[52] U.S. Cl. ...................................... 585/660; 585/654
[58] Field of Search ................................. 585/654, 660

[56] References Cited

U.S. PATENT DOCUMENTS 3,461,183 8/1969 Hepp et al. ........................... 585/660
3,880,776 4/1975 Box, Jr. et al. ....................... 252/466
4,902,849 2/1990 McKay et al. ....................... 585/660
4,926,005 5/1990 Olbrich et al. ....................... 585/654

Primary Examiner—Curtis R. Davis
Attorney, Agent, or Firm—Charles W. Stewart

[57] ABSTRACT

A method for improving the activity of a dehydrogenation and dehydrocyclization catalyst composition and a process for improving the conversion and selectivity of paraffin hydrocarbons to olefin and aromatic compounds. The novel processes comprise adding calcium aluminate to a catalyst composition comprising a zinc aluminate support and a catalyst metal, and optionally a promoter metal.

12 Claims, 3 Drawing Sheets

CATALYST AND PROCESS FOR DEHYDROGENATION AND DEHYDROCYCLIZATION

This invention relates to catalytic dehydrogenation and dehydrocyclization of organic compounds. In another aspect, it relates to dehydrogenation and dehydrocyclization processes. In yet another aspect, it relates to dehydrogenation and dehydrocyclization catalysts.

In recent years, the composition of the motor gasoline pool has dramatically been altered due to changes in environmental regulations. Because of regulations limiting the allowable maximum gasoline vapor pressure, the amount of high vapor pressure components such as butane that can be blended in gasoline must be reduced in order for final gasoline products to meet the various vapor pressure requirements dictated by regulation. Consequently, these gasoline vapor pressure limitations have resulted in an increased supply availability of high vapor pressure butanes due to their removal from the gasoline pool.

In addition to the vapor pressure regulations, there have also been a number of other regulations which have contributed to the reduction of high octane components available for use in the gasoline pool. For instance, limits on the amount of lead additive which may be used in gasoline have resulted in the removal of substantial quantities of octane from the gasoline pool. Further proposed regulations, such as the limitations on the quantity of high octane aromatic compounds that may be mixed in gasoline, may also impact the amount of octane available for use in the gasoline pool. There are numerous other factors contributing to the reduction in available octane.

One possible response to the changing composition of the gasoline pool is for industry to dehydrogenate low molecular weight alkanes to alkenes that can be used as a feedstock in downstream processes, such as the HF alkylation and methyl tertiary butyl ether (MTBE) processes, by which high octane, low vapor pressure gasoline blending components can be produced. A further response is to dehydrocyclize low octane, light paraffins to high octane aromatics. The production of MTBE, which involves reacting the isobutylene produced from the dehydrogenation process with methanol, provides a source of oxygen in gasoline when used as a gasoline blending component thereby helping to meet the various regulations which may require the addition of oxygen compounds. Furthermore, by removing butanes from the gasoline pool and dehydrogenating them to form butenes that are used as feedstocks to downstream operations, high vapor pressure gasoline components are removed from the gasoline pool and are replaced with low vapor pressure, high octane components.

There are numerous approaches known for the dehydrogenation of organic compounds. One such approach is the non-catalytic thermal dehydrogenation of organic compounds. However, this method of dehydrogenation has not been commonly accepted because of the extensive undesirable side reactions and substantial coke production which take place. Thus, it has been sought to develop a catalytic dehydrogenation and dehydrocyclization process that provides a high conversion of feedstock and high selectivity to desirable end-products. To accomplish this, a vital aspect of the process is the use of a catalyst having certain desirable properties. Some of these desired properties are that the catalyst have the ability to convert a large fraction of a given feed material to end-products and that the conversion be highly selective in producing certain desired end-products. In using a catalyst that gives a high conversion per pass, energy costs associated with a given process can be lowered by reducing the cost of separation and recycling of the unconverted feed material. In addition, a highly selective catalyst will improve the operating efficiency of the process by reducing the amount of unwanted end-products produced.

In the dehydrogenation and dehydrocyclization processes, considerable advantages are obtainable when hydrocarbon feed to the reactor can be diluted with steam. The mixing of the hydrocarbon feed with steam has the effect of lowering the partial pressure of the hydrogen produced from the reaction and that of the hydrocarbon thus shifting the equilibrium conditions within the reactor toward greater conversion of the feedstock. Additional benefits from the use of steam are that it can provide a portion of the heat of reaction required and it can retard the rate of coke deposition on the catalyst. Furthermore, expensive compression of products can be avoided since elevated pressures can be employed and steam can be readily condensed after dehydrogenation is effected. Because of the great advantages possible from using a steam diluent in the dehydrogenation and dehydrocyclization of hydrocarbons, attempts have been made to develop catalysts which have high stability to steam and that allow dehydrogenation of alkanes in the presence of steam.

There are numerous other desirable catalyst properties which contribute to the improved performance and design of a dehydrogenation and dehydrocyclization processes. Among these is a catalyst having high crush strength. The higher the crush strength of the catalyst the more durable the catalyst and the greater the amount of pressure drop which can be experienced in a bed reactor without damaging the catalyst. Moreover, the useful life of a catalyst may be increased.

It is, therefore, an object of this invention to provide an improved dehydrogenation and dehydrocyclization process.

It is another objective of this invention to provide an improved dehydrogenation and dehydrocyclization catalyst.

I have discovered a novel method for improving the activity and selectivity of a catalyst composition used in the dehydrogenation and dehydrocyclization of steam-diluted hydrocarbons. It has been found and demonstrated herein that it is a critical element of this invention to have the presence of calcium aluminate in the catalyst support of dehydrogenation and dehydrocyclization catalyst. The standard support formulation of the prior art included a 100 percent zinc aluminate support, but, the composition was not suitable for commercial use. It has been found that new and material beneficial properties that are different from those disclosed in the prior art are achievable by the incorporation of calcium aluminate into the support material of this invention. Unexpectedly, by the addition of calcium aluminate to a dehydrogenation or dehydrocyclization catalyst supported by zinc aluminate, the percent conversion of saturated hydrocarbons to unsaturated hydrocarbons is substantially improved. The presence of calcium aluminate as a support accounts for an overall improvement in activity of the catalyst composition. Additionally, it has been discovered that the method herein results in a longer lived catalyst activity than those lives shown in the art.

The novel method for improving the activity of a dehydrogenation or dehydrocyclization catalyst is generally performed by combining with a support composition comprising zinc aluminate and certain Group VIII metals as a catalyst, calcium aluminate in any manner known to the art; and, optionally, certain Group IA, Group IIA, Group IIB, lead, tin, germanium, gold or silver as promoters of the activity of the supported Group VIII metal catalyst. This invention further includes a process for the dehydrogenation and dehydrocyclization of hydrocarbon utilizing the novel step of adding calcium aluminate to a catalyst composition for the purpose of improving conversion and selectivity.

Other objects, aspects, and features of the present invention will be evident from the following detailed description of the invention, the claims and the drawings in which:

Figure 1:
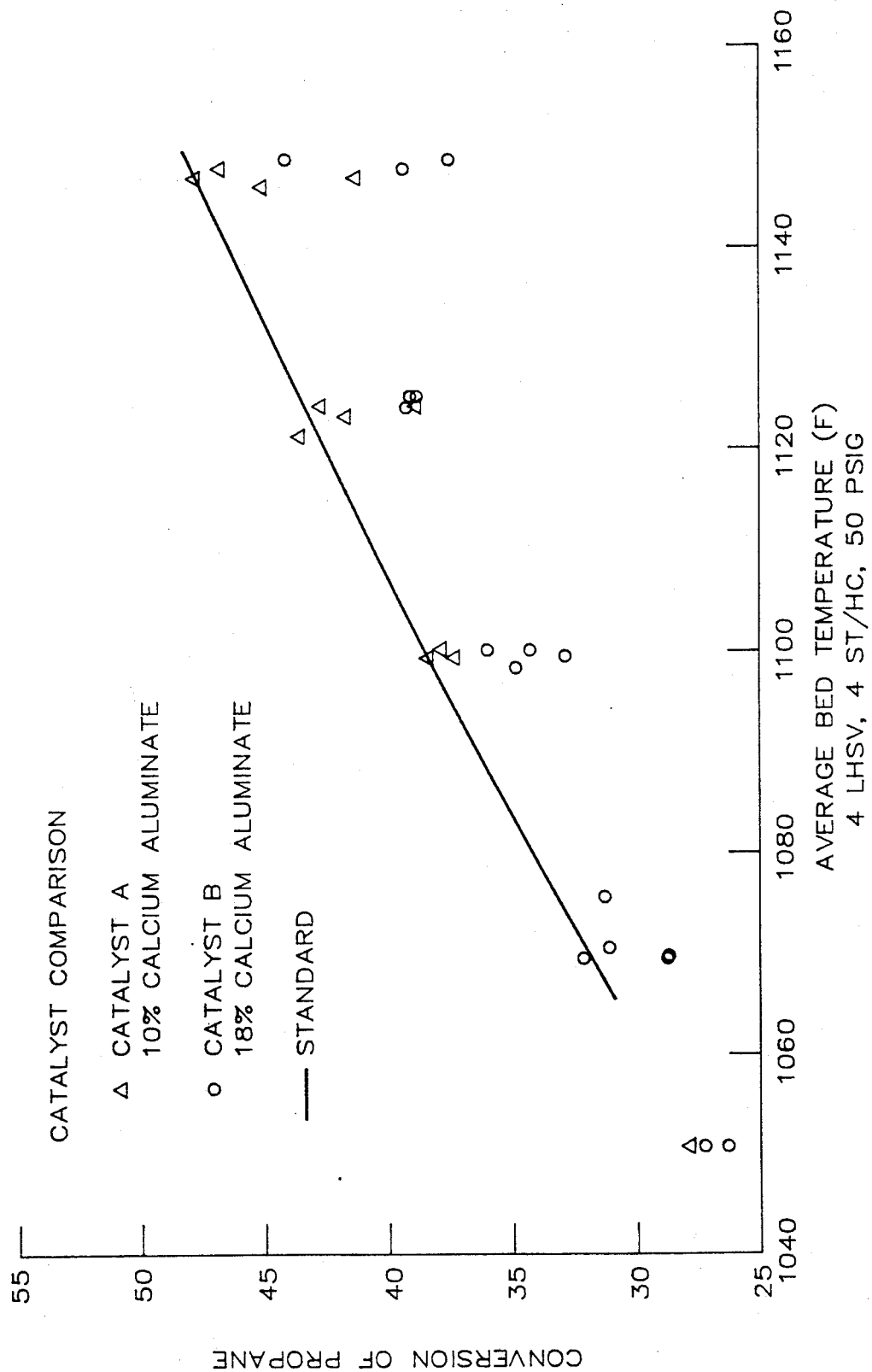
FIG. 1 is a graphical diagram comparing propane conversion as a function of temperature for three different catalyst compositions, which includes the novel catalyst composition of the present invention.

The catalyst activity and selectivity of this invention can be improved by combining in any manner known to the art, certain Group VIII metals or metal compounds capable of reduction to the metal and mixtures of two or more thereof and zinc aluminate with calcium aluminate. As used herein, the term Group VIII metals, or similar language, specifically include iron, cobalt, nickel, ruthenium, rhodium, palladium, osmium, iridium, and platinum. Platinum, which is very effective, is preferred. The Group VIII metal content of the catalyst can be in the range of from about 0.01 to about 5 weight percent of the support and, in a preferred embodiment, it is in the range of from about 0.1 to about 1 weight percent of the support. Throughout this application the term "weight percent of the support" means parts by weight per 100 parts by weight of support material.

Any platinum group metal compound that produces the desired results can be used. In the discussion of the compounds that can be used, the platinum compounds will be used as nonlimiting examples. It is to be understood that similar compounds of the other platinum group metals can be used. Examples of simple or non-coordination compounds that can be used are platonic chloride, chloroplatinic acid, ammonium chloroplatinate, and the like. Nonlimiting examples of coordination platinum compounds that can be used are: platinum amminoacetate, platinum dimethyl dioxime, tetraammineplatinum hydroxide, platinum diammine dinitrate, platinum tetraammine dihydroxide, platinum diammine dihydroxide, platinum hexammine dihydroxide, platinum hexammine tetrahydroxide, platinum diammine tetrahydroxide, platinum diammine dihydroxide dinitrate, platinum diammine tetranitrate, platinum diammine dinitrite, platinum tetraammine dicarbonate, platinum diammine oxalate, and the like. Additionally, many complex or coordination divalent and tetravelent platinum compounds are known and can be used.

When added to the support by impregnation from solution, some of the compounds can be added from aqueous solution, but others will require non-aqueous solvents such as alcohols, hydrocarbons, ethers, ketones and the like.

In addition to the Group VIII metals, the catalyst composition can contain a tin group metal including lead, tin, germanium and mixtures of two or more thereof as a promoter. The tin component can be deposited with the Group VIII metal component upon the catalyst support, separately or together, by any manner known in the art such as by deposition from aqueous and non-aqueous solution of tin halides, nitrates, oxalates, acetates, oxides, hydroxides and the like. The tin group metal can exist in the range upwardly to about 5 weight percent of said support and, in a preferred embodiment, it can exist in the range of from about 0.1 to about 1.5 weight percent of said support.

Although any tin group metal in compound form is fully within the scope of this invention, some convenient tin group compounds are the halides, nitrates, oxalates, acetates, carbonates, propitiates, tartrates, bromates, chlorates, oxides, hydroxides, and the like of tin, germanium and lead. Tin, itself, is the preferred tin group metal and impregnation of the catalyst support with tin compounds such as the stannous halidex is particularly effective and convenient.

Also, in addition to the Group VIII metals, the catalyst composition can further include, with or without the tin group metal, a Group IA or Group II metal or metal compound as a promoter. This can be conveniently done by conventional impregnation. The amount of each alkali metal compound or combination of compounds can exist in the range upwardly to about 5 weight percent of the support; however, in a preferred embodiment, a range from about 0.1 to about 1 weight percent of said support is used. Convenient compounds which can be used are the carbonates, acetates, and hydroxides and the like of sodium, barium, potassium, calcium, and the like.

Another promoter metal which can be used in an embodiment of this invention, is a metal selected from the group consisting of gold, silver and mixtures thereof. This promoter metal may or may not be used in combination with the tin group promoter metals, Group IA, or Group II promoter metals. The amount of gold, silver or mixtures of such to be used as a promoter is in the approximate range of from about 0.1 to about 5 weight percent of the support. Suitable gold and silver compounds include, but are not limited to, arsinic chloride, arsinic sulfate, aurous chloride, tetrachlorauric acid, silver nitrate, silver acetate, silver cyanide and the like.

The support material of this invention comprises a mixture of zinc aluminate and calcium aluminate. The support can be prepared by any method known in the art. While the prior art teaches that the most effective support composition is zinc aluminate, the novel method of this invention gives a catalyst, when included with the Group VIII metals or promoter metals, or both, having greater activity and selectivity than those of a catalyst using exclusively a zinc aluminate support. A further advantage from having a catalyst support mixture of zinc aluminate and calcium aluminate is that the addition of calcium aluminate improves the crush strength of the base material.

Any suitable amount of calcium aluminate can be present in the support material. In a preferred embodiment, calcium aluminate is added so as to be present in the range of from about 5 weight percent to about 25 weight percent of the support. Most preferably, the content of calcium aluminate is in the range of from about 10 weight percent to about 18 weight percent.

The 25 weight percent content limitation for the presence of calcium aluminate appears to be a critical limit for this component of the novel composition. As the presence of calcium aluminate increases, it becomes increasingly more difficult to regenerate the composition once it has become spent; however, the greater the proportion of the composition that is calcium aluminate the greater the activity and selectivity of the composition. Additionally, the crush strength of the composition is improved with increasing amounts of calcium aluminate present. When accounting for these newly discovered beneficial properties of the composition that are obtainable by the addition of calcium aluminate along with the negative effects associated with the addition of calcium aluminate, the 25 weight percent limitation appears to be close to the maximum permissible amount of calcium aluminate that can be present while still giving a composition having the desireable properties of improved crush strength and improved catalyst activity and selectivity.

Improved dehydrogenation and dehydrocyclization processes are achieved by the use of the novel step of adding calcium aluminate to a composition comprising zinc aluminate and a catalyst metal prior to a contacting step. In these processes, paraffins containing five carbons or less are dehydrogenated to the respective olefin compounds, and paraffins containing six or more carbon atoms can be dehydrocyclized to cyclic and aromatic compounds or they can be dehydrogenated to olefin compounds. In a preferred embodiment of this invention, paraffin hydrocarbons are first preheated and vaporized and mixed with steam with the thus formed mixture being passed over a bed of the novel catalyst composition of this invention. The mole ratio of steam mixed with the hydrocarbon can be in the range of from about 2 to about 30 moles of steam per mole of hydrocarbon; preferably, however, the mole ratio will be in the range of from about 2 to about 10. The presence of steam as a diluent provides a benefit by reducing the partial pressure of the hydrocarbons and hydrogen present in the reactor and thereby shifting the equilibrium conditions within the reactor toward greater conversion of the hydrocarbons.

A preferred approach to utilizing the inventive process is to pass the vaporized, steam diluted hydrocarbon through either a single or a plurality of fixed bed tube reactors. Because the dehydrogenation reaction is generally an endothermic reaction, to maintain a near isothermal reaction, heat must be added. It has been found that the most favorable reaction kinetics can be achieved by operating the reactor non-adiabatically. In this mode of operation, it is preferred that the reactor be of the tubular type with the heat source being external to the tubes of the reactor which may, for example, be the firebox of a gas fired heater. Any number of tube reactors may be used, but it is preferred that a multiplicity of tubes be used where one or more tubes may be removed from service for the purpose of regeneration of the catalyst simultaneously while the other tubes remain in operation. One design configuration using the novel process of this invention is to have eight reactor furnaces each of which is associated and operated in conjunction with a reactor section. Each reactor section can include a plurality of as many as 150 individual reactor tubes. Of the eight reactor sections, it is preferred that seven of the reactor operating sections be in operation while one of the reactor sections is simultaneously undergoing regeneration.

The dehydrogenation reactor operating conditions are set so as to optimize the process by taking into account such factors as the type of feedstock being processed, operating costs, product values, and product yields. Typically, it is advantageous to feed the reactors at a rate which gives a liquid hourly space velocity (LHSV) ranging from about 0.5 to about 10 volumes of liquid hydrocarbon feed per hour per volume of catalyst. For computing the value for liquid hourly space velocity, the volume of liquid hydrocarbon is determined at standard conditions of 60° F. and atmospheric pressure, and the volume of catalyst is determined by the volume of the catalyst contained within the reactor vessel. The reactor pressure can range from below atmospheric pressure to about 300 psia. It is preferred, however, to minimize the operating pressure of the reactor in order to improve conversion, but an advantage from operating the reactor at higher operating pressures is that the compression ratio of the downstream reactor effluent compression can be minimized by a higher operating pressure thereby providing certain design and operating benefits. The optimum operating pressure is determined by taking into account all these considerations. As for the reactor temperature, it can range from about 900° F. to about 1150° F. depending upon the type of hydrocarbon being processed and other constraints. Generally, the higher the operating temperature the greater the conversion.

The reactor effluent is passed through a feed/effluent heat exchanger or a series of feed/effluent heat exchangers in which heat contained within the reactor effluent stream is exchanged with incoming hydrocarbon feed that is being charged to the tube reactors. After passing through the feed/effluent exchangers, the reactor effluent is passed through a steam section in which superheated steam is produced for use in a steam expander. The reactor effluent leaving the steam generation section is optionally passed through a reboiler exchanger followed by an exchange of heat with incoming hydrocarbon feed in the feed preheat section. The use of a reboiler exchanger will depend upon the feedstock to the process. The process effluent is further transferred through a series of phase separators and heat exchangers where condensate is separated from the hydrocarbons and uncondensed steam and is returned to the steam generation section for reuse. The final vaporous product effluent is compressed prior to being charged to a recovery system where the final olefin and aromatic products, light ends, and hydrogen are recovered. In the recovery system, hydrogen gas can optionally be recovered by any suitable means, including, for example, separation membranes, lean oil/rich oil systems, cryogenic processes and pressure swing absorption systems, depending upon the economic value of the hydrogen and its potential downstream uses. The light ends recovered and any unrecovered hydrogen can be used as a fuel source in the reactor furnace. The final end-product is treated and sent to storage or to other downstream processes.

Other objects, aspects, and features of the present invention will be evident from the following example.

EXAMPLE I

Two catalyst formulations for dehydrogenation or dehydrocyclization, or both, were prepared for pilot plant testing and for comparison with dehydrogenation catalyst having essentially a 100 percent zinc aluminate support. Presented in Table I are the compositions of the two catalysts tested and the analysis of the 100 percent zinc aluminate comparison catalyst. Catalyst A was formulated by mixing 10 percent calcium aluminate and 90 percent zinc aluminate, and catalyst B was formulated by mixing 18 percent calcium aluminate and 82 percent zinc aluminate. The calcium aluminate used in catalyst A was a commercially produced product of Lone Star Lafarge, Inc. known by its tradename Secar® 71 calcium aluminate. The calcium aluminate used in catalyst B was a commercially produced product of Alcoa® known by its tradename CA-25 calcium aluminate. The two calcium aluminates are produced by different manufacturing techniques and have slightly different compositions which may account for some of the differences in the properties between catalyst A and catalyst B as hereinafter is described. The zinc aluminate used in all catalyst was prepared by mixing zinc oxide (ZnO) with a fumed alumina ($Al_2O_3$), which is manufactured and is commercially available from Degussa Corporation as its product known as aluminum oxide C, and calcining the mixture at a temperature of about 1550° F. for a period of five hours. Each catalyst base was impregnated by conventional means with platinum metal catalyst and a tin metal promoter. The resulting catalyst was formed into 4–8 mesh catalyst pellets and packed into a two-inch diameter reactor equipped with thermocouples for measuring the reactor bed temperature and for obtaining an axial and a radial temperature profile within said bed.

TABLE I

|  | Comparison Catalyst 100% Zinc Aluminate | Catalyst A (10% Secar 71) Calcium Aluminate | Catalyst B (18% CA-25) Calcium Aluminate |
| --- | --- | --- | --- |
| Aluminum (Al) |  | 28.5 | 28.1 |
| Calcium (Ca) |  | 1.3 | 2.0 |
| Zinc (Zn) |  | 33.0 | 30.0 |
| Platinum (Pt) | 0.6 | 0.51 | 0.55 |
| Tin (Sn) | 1.0 | 1.0 | 0.9 |
| Pore Volume cc/gm |  | 0.54 | — |
| Surface Area m$^2$/g |  | 29.0 | 31.5 |
| Skeletal Density g/cc |  | 4.29 | 4.29 |
| Crush Strength (lb) | 7.2 | 28.6 | 16.5 |
| Mercury Poresimetry Data: |  |  |  |
| Pore Area m$^2$/g |  | 71.0 | 89.4 |
| Ave Pore Diam A |  | 406 | 208 |
| Bulk Density g/cc |  | 1.59 | 1.51 |
| Skeletal Density g/cc |  | 5.55 | 5.12 |
| Median Pore Diameter (Vol) A |  | 406 | 343 |
| Median Pore Diameter (Area) A |  | 169 | 131 |

A series of propane dehydrogenation tests were performed using the catalyst described in Table I. In performing the test runs, superheated steam at a temperature of approximately 1300° F. was mixed with propane having an approximate temperature of 600° F. The ratio of steam-to-hydrocarbon was maintained at approximately a 4 to 1 ratio. Prior to charging this mixture to the reactor, it was passed through a final trim heater to bring the temperature up to the desired reaction temperature. The volumetric charge rate to the reactor was set so as to give a liquid hourly space velocity (LHSV) of 4 volumes of hydrocarbon feed per volume of catalyst per unit time with the time unit as hours. The reactor pressure was maintained at 50 psig by a pressure control valve placed at the outlet of the reactor. The reactor temperature was set at various temperatures to generate conversion and selectivity data of propane to propylene for comparison with the different catalyst compositions.

Figure 2:
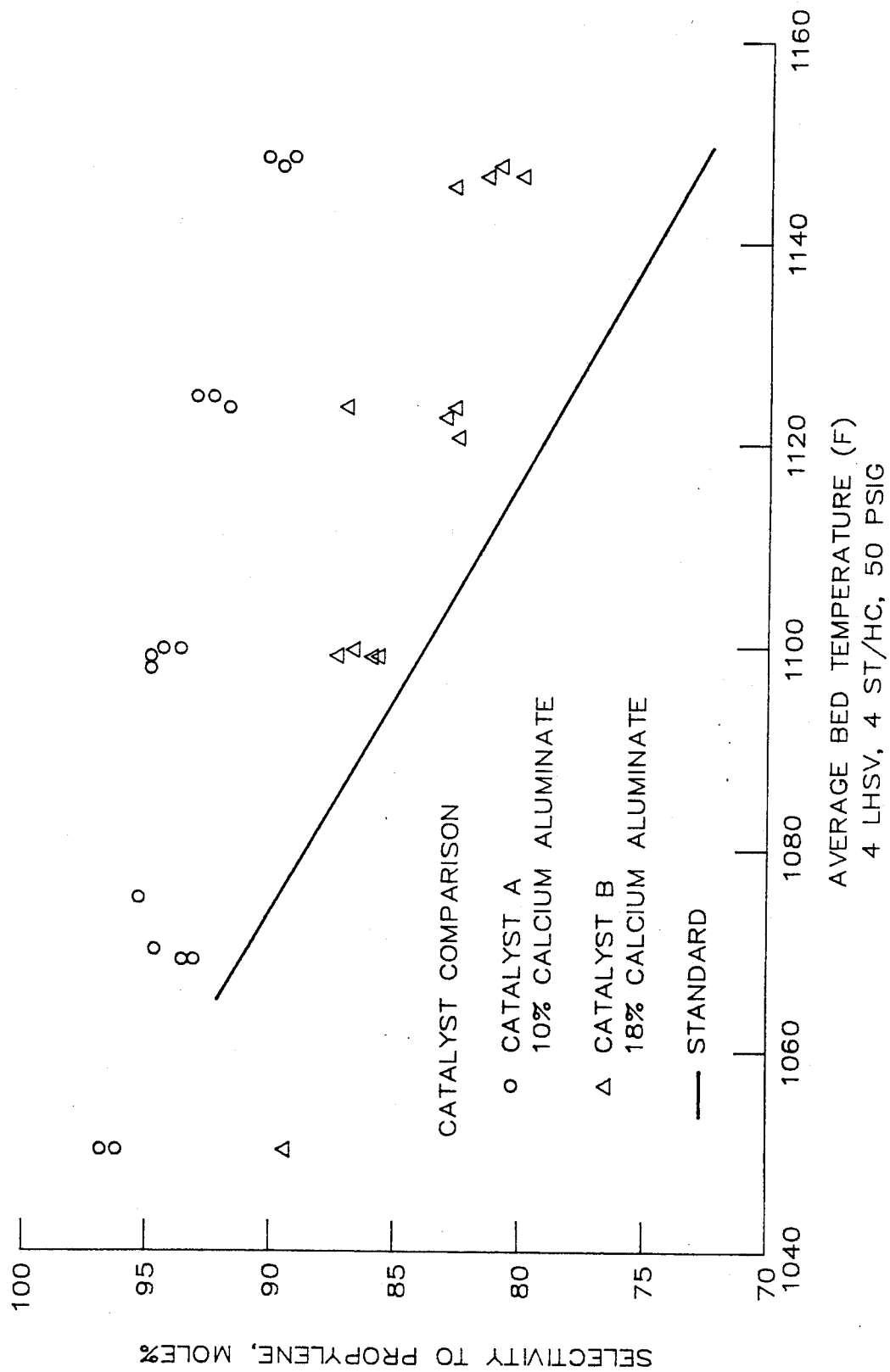
FIG. 2 is a graphical diagram comparing propylene selectivity as a function of temperature for three different catalyst compositions, which includes the novel catalyst composition of the present invention.
Figure 3:
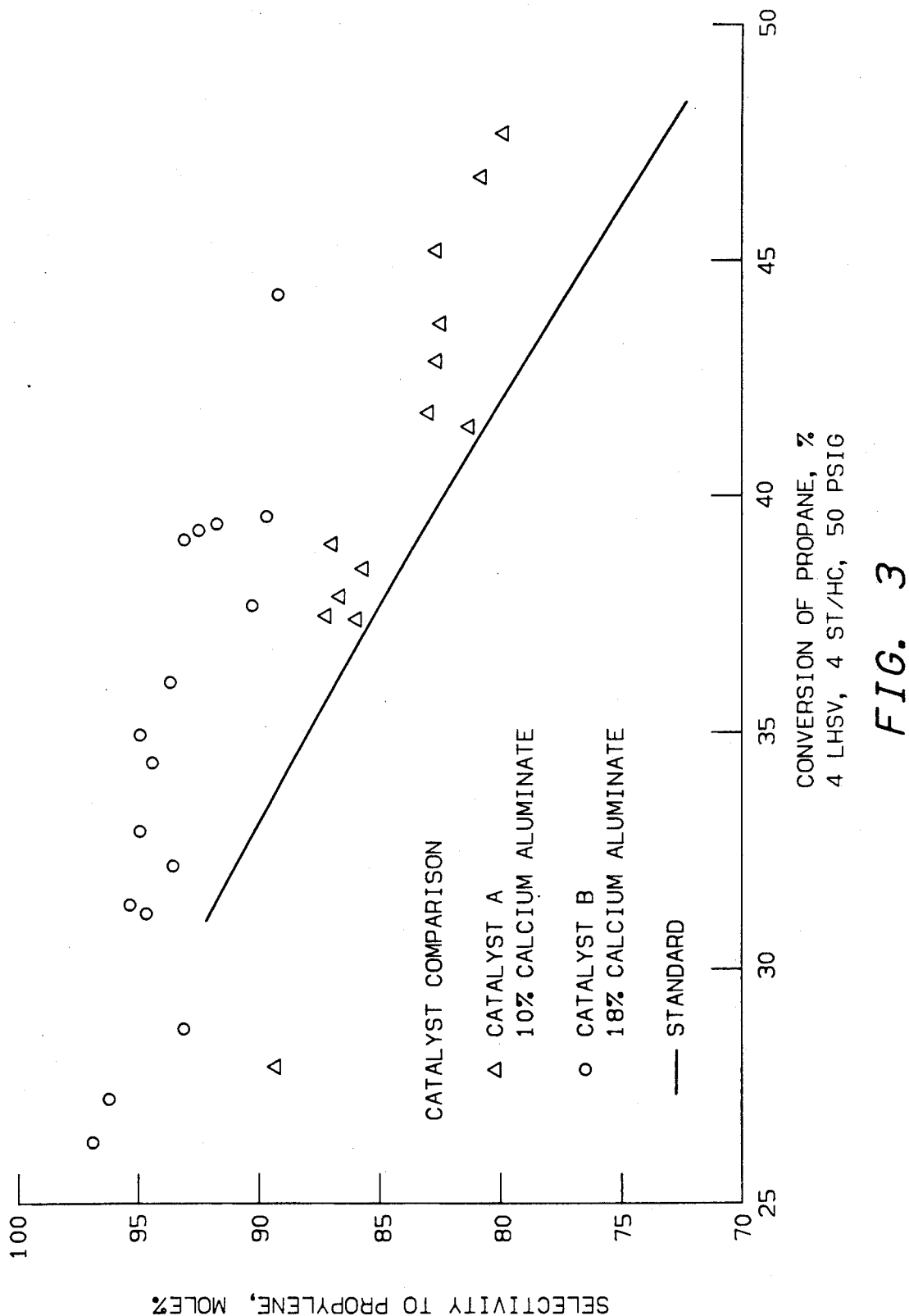
FIG. 3 is a graphical diagram comparing propylene selectivity as a function of conversion for three different catalyst compositions, which includes the novel catalyst composition of the present invention.

FIGS. 1, 2 and 3 are provided to graphically present the test run results and show a comparison of the test results for the novel catalyst compositions with the standard 100 percent zinc aluminate support catalyst. The solid lines on each FIG. represents the predicted performance of the standard catalyst based upon an empirical statistical model developed from data generated from eighty-three test runs using the 100 percent zinc aluminate support catalyst. The data points on each FIG. show the test run results for Catalyst A and for Catalyst B. FIG. 1 shows the percent conversion of propane as a function of average reactor bed temperature for each of the three catalysts tested. As can be seen from the data, conversion increases with increasing temperature. The relationship between propane selectivity to propylene and reactor temperature for each of the three catalysts is presented in FIG. 2. FIG. 2 shows that, generally, at a given reactor temperature, Catalyst A and Catalyst B both give a higher percent selectivity than the standard catalyst. FIG. 3 shows the relationship between the selectivity of each of the three catalysts and conversion. Generally, at a fixed percent propane conversion, both Catalyst A and Catalyst B give a higher percent selectivity than the standard catalyst.

The test results unexpectedly show that the selectivity of the dehydrogenation of propane to propylene can be improved by using a catalyst having a mixture of calcium aluminate and zinc aluminate support rather than the traditional catalyst support mixture of 100 percent zinc aluminate. The catalytic selectivity improves as the amount of calcium aluminate is increased, however above about 25 weight percent calcium aluminate, the catalyst becomes increasingly difficult to regenerate. It is believed that catalyst A and B represent near optimum mixtures balancing improved performance with suitable regeneration characteristics.

Reasonable variations and modifications may be made in the combination and arrangement of parts or elements or in the processes as heretofor set forth in the specification and shown in the drawings without departing from the spirit and scope of the invention as defined in the following claims.

That which is claimed is:

1. In a process wherein hydrocarbons are contacted with a catalyst composition comprising a zinc aluminate support and a metal catalyst selected from the group consisting of Group VIII metals, the improvement comprising:
   adding calcium aluminate to said zinc aluminate support in the amount in the range of from about 5 to about 25 weight percent, based upon the total combined weight of said zinc aluminate and said calcium aluminate; and
   recovering a reactor effluent product.

2. A process as recited in claim 1, further including:
   preheating said hydrocarbons prior to contacting with said catalyst composition.

3. A process as recited in claim 2, further including:

mixing said preheated hydrocarbons with steam prior to contacting with said catalyst composition.

4. A process as recited in claim 3, further including:
cooling said reactor effluent to form a condensate phase and a vapor phase, and separating said condensate phase and said vapor phase.

5. A process as recited in claim 4, further including:
compressing said vapor phase.

6. A process as recited in claim 5, further including:
recovering a hydrogen product, a light ends product and a hydrocarbon product from the thus compressed vapor phase.

7. A process as recited in claim 1 wherein:
said hydrocarbons comprise compounds having from 3 to 8 carbon atoms.

8. A process as recited in claim 1 wherein:
said contacting step is performed in a temperature range from 900° F. to 1150° F.

9. A process as recited in claim 1 wherein:
said contacting step is performed at a pressure from below atmospheric pressure to 310 psia.

10. A process as recited in claim 1 wherein:
said hydrocarbons are mixed with steam at a mole ratio of from 2 to 30 prior to contacting the thus formed mixture with said catalyst composition.

11. A process as recited in claim 1 wherein:
said hydrocarbons are contacted with said catalyst composition at a rate to give a liquid hourly space velocity of from about 0.5 to about 10.

12. In a process wherein hydrocarbons having from 3 to 8 carbon atoms are contacted with a catalyst composition comprising zinc aluminate support and a metal catalyst selected from the group consisting of Group VIII metals and mixtures of two or more thereof, the improvement comprising:
adding calcium aluminate to said catalyst composition in the amount of about 10 to 18 weight percent, based upon the total combined weight of said zinc aluminate and said calcium aluminate, wherein said hydrocarbons are admixed with steam in a mole ratio of steam to hydrocarbon in the range of from about 2 to about 30 at dehydrogenating conditions wherein the temperature range is of from about 900° F. to about 1150° F., the pressure range is of from below atmospheric pressure to about 300 psia, and the liquid hourly space velocity is in the range of from about 0.5 to about 10.

* * * * *